Figure 1:
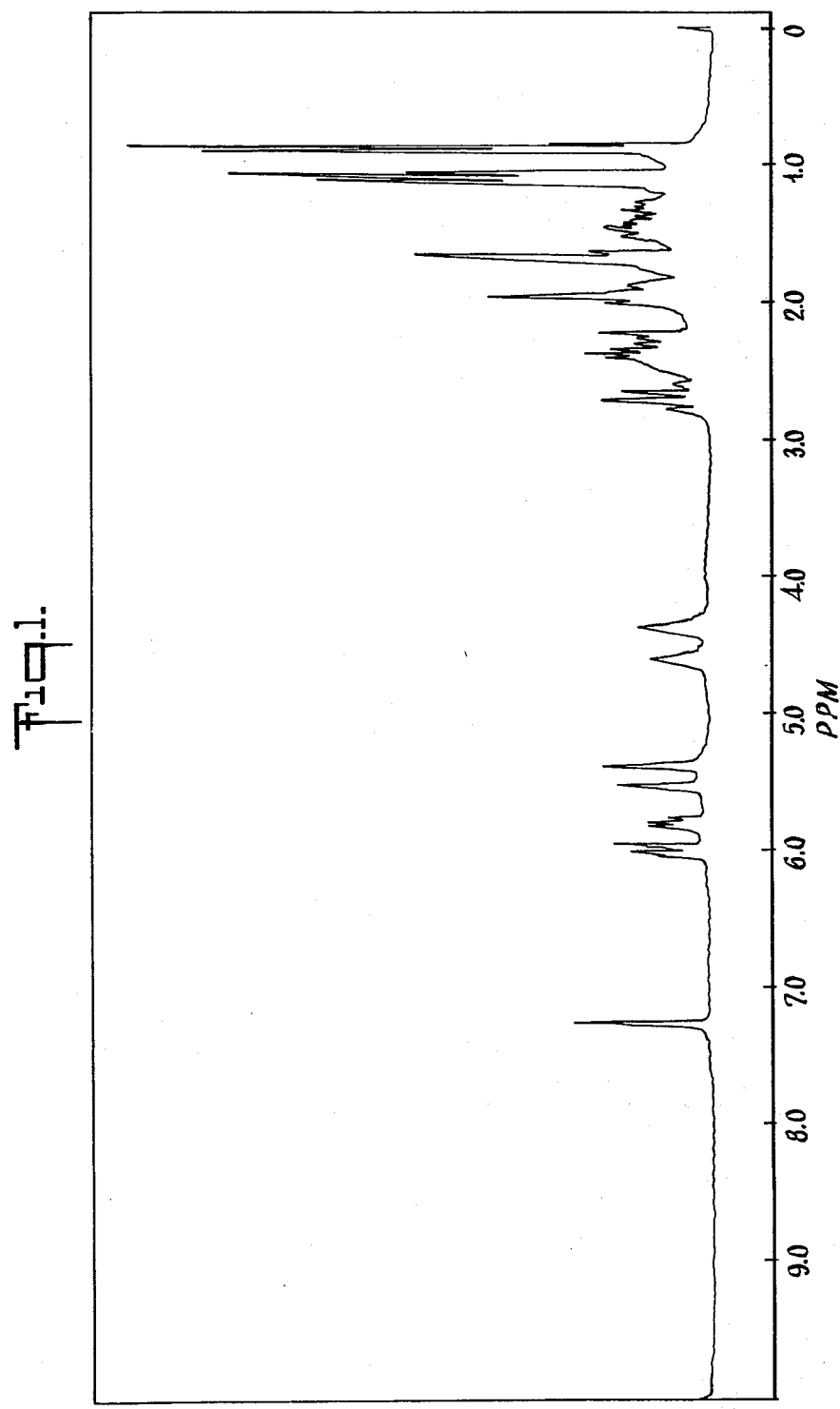
Figure 2:
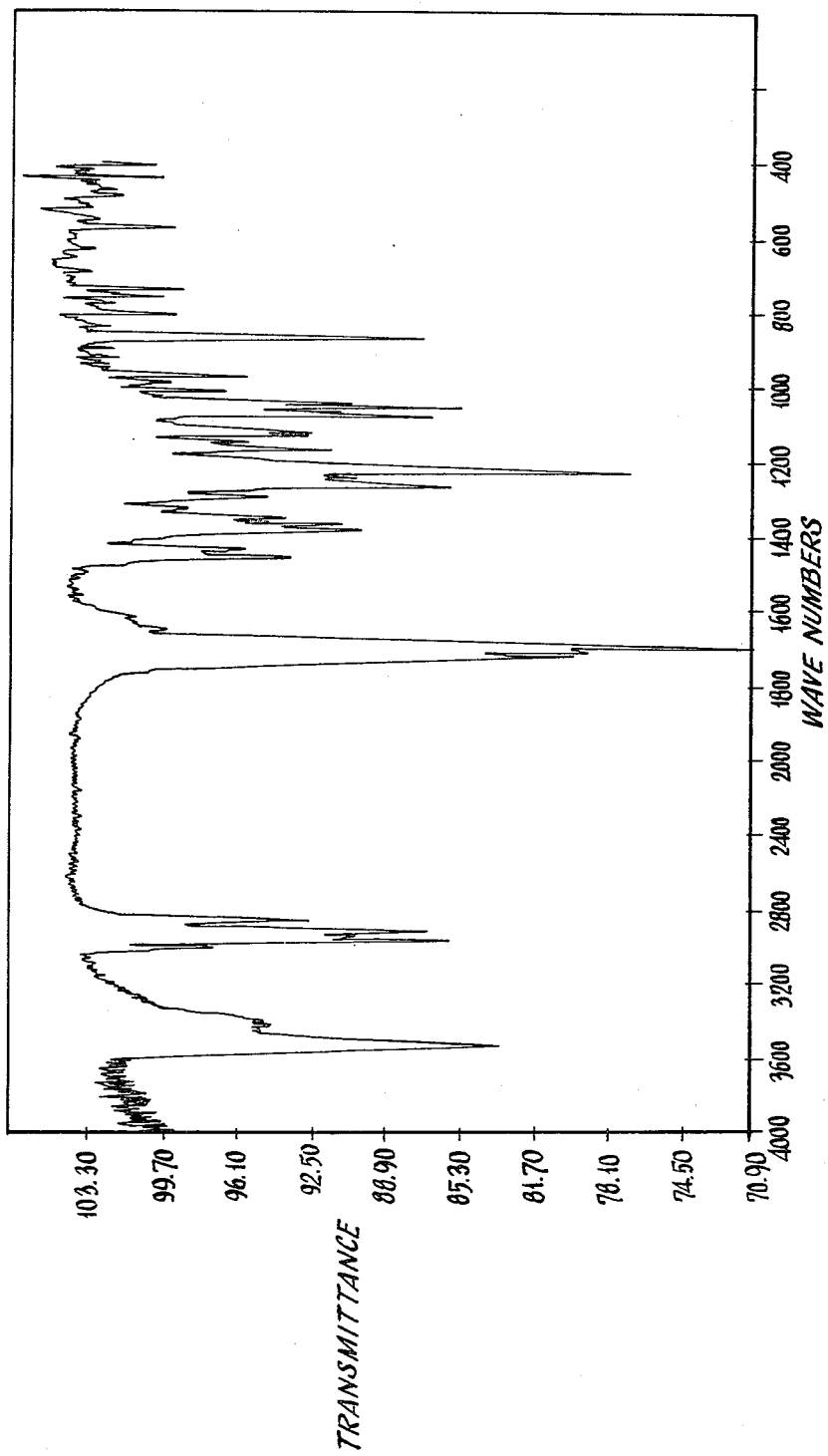

United States Patent [19]

Monaghan et al.

[11] 4,294,926
[45] Oct. 13, 1981

[54] HYPOCHOLESTEREMIC FERMENTATION PRODUCTS AND PROCESS OF PREPARATION

[75] Inventors: Richard L. Monaghan, Somerset; Alfred W. Alberts, Short Hills; Carl H. Hoffman, Scotch Plains; George Albers-Schonberg, Princeton, all of N.J.

[73] Assignee: Merck & Co., Inc., Rahway, N.J.

[21] Appl. No.: 114,458

[22] Filed: Jan. 23, 1980

Related U.S. Application Data

[62] Division of Ser. No. 48,946, Jun. 15, 1979, Pat. No. 4,231,938.

[51] Int. Cl.³ .............................. C12P 7/26; C12P 17/06
[52] U.S. Cl. ..................................... 435/125; 435/135; 435/136; 435/148; 435/913
[58] Field of Search ............... 435/125, 171, 913, 148, 435/135, 146, 136

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 435/125 |
| 4,137,322 | 1/1979 | Endo et al. | 424/273 R |

OTHER PUBLICATIONS

Endo et al., *Eur. J. Biochem.*, 77, 31–36 (1977).

Endo et al., *The Journal of Antibiotics*, XXIX (12), 1346–1348 (1976).
Endo et al., *FEBS Letters*, 72(2), 323–326 (1976).
Brown et al., *J.C.S. Perkin I*, 1165–1169 (1976).

*Primary Examiner*—Esther M. Kepplinger
*Attorney, Agent, or Firm*—William H. Nicholson; Mario A. Monaco

[57] ABSTRACT

Substances isolated after cultivation of a microorganism belonging to the genus Aspergillus in a culture medium comprise a compound designated MSD803 which has the lactone structure:

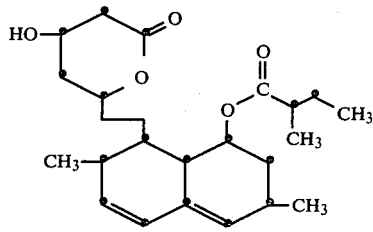

as well as its free hydroxy acid form. Together with salts and esters of the free acid form, these compounds form a class of highly active hypocholesteremic and hypolipemic medicaments.

3 Claims, 2 Drawing Figures

HYPOCHOLESTEREMIC FERMENTATION PRODUCTS AND PROCESS OF PREPARATION

This is a division of application Ser. No. 48,946, filed June 15, 1979, now U.S. Pat. No. 4,231,938.

SUMMARY OF THE INVENTION

This invention relates to hypocholesteremic products from the cultivation of a microfungus of the genus Aspergillus. More specifically, it relates to a compound of the formula:

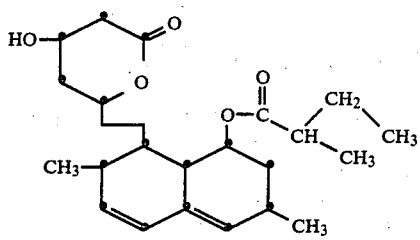

and to the corresponding free hydroxyacid

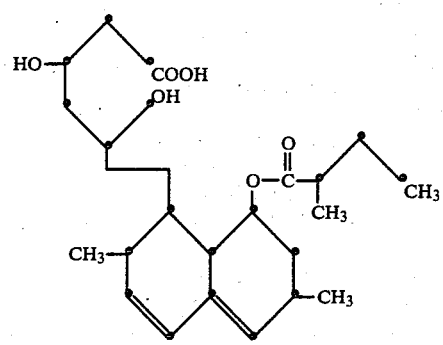

As well as pharmaceutically acceptable salts of the latter and lower alkyl and substituted alkyl esters of the latter in which the possible substituent is phenyl, dimethylamino or acetylamino. The invention also relates to a process of cultivating the microfungus and isolating from the medium a hypocholesteremic compound of the above structures. These new compounds have excellent properties of inhibiting cholesterol biosynthesis and are useful against hypercholesteremia and hyperlipemia.

BACKGROUND OF THE INVENTION

Because of the possible connection between high blood cholesterol and atherosclerosis, many efforts have been made to find ways and substances which would reduce the cholesterol in the mammalian body. One of these ways is to inhibit in mammals the body's ability to synthesize cholesterol.

Recently, Endo et al., described (U.S. Pat. No. 3,049,495 and 3,983,140) a fermentation product obtained by cultivation of a microorganism of the genus Penicillium and isolation from the medium. They called it ML 236 B and determined its structure together with two related compounds 236.A and 236 C. Its structure, under the name compactin, was also determined by A. G. Brown, T. C. Smale, T. J. King, J. Chem. Soc. (Perkin I) 1165 (1975). This compound has been found to be a strong inhibitor in vivo of the biosynthesis of cholesterol.

DESCRIPTION OF THE INVENTION

We have found that unexpectedly, the cultivation of a very different microorganism, a microfungus of the genus Aspergillus, produces a new substance that is also a very potent inhibitor of the biosynthesis of cholesterol in mammals. We have further found that this substance comprises principally the new compound, MSD803, of the above structure, accompanied by only traces of other compounds, none of which appears to be those isolated by Endo et al. This new compound of our invention does not appear to be formed in the fermentations described by Endo. The new compound, MSD803, is a much more potent inhibitor of cholesterol synthesis in vivo than is the compound, ML236B described by Endo.

The compounds of this invention are highly useful as antihypercholesteremic agents for the treatment of atherosclerosis, hyperlipemia and like diseases in humans. They may be administered orally or parentally in the form of a capsule, a tablet, an injectable preparation and the like. It is usually desirable to use the oral route. Doses may be varied, depending on the age, severity, body weight and other conditions of human patients but daily dosage for adults is within a range of from about 2 mg. to 2000 mg. (preferably 10 to 100 mg.) given in three or four divided doses. Higher doses may be favorably applied as required.

The compounds of this invention also have useful antifungal activities. For example, they may be used to control strains of Penicillium sp., Aspergillus niger, Cladosporium sp., Cochliobolus miyabeorus and Hilminthosporium cynodnotis. For those utilities they are admixed with suitable formulating agents, powders, emulsifying agents or solvents such as aqueous ethanol and sprayed or dusted on the plants to be protected.

In another aspect of this invention, it relates to a process for producing the compounds of this invention which comprises cultivating a microorganism belonging to the genus Aspergillus and then recovering said compounds of this invention from the cultured broth. Based upon taxonomic studies, this Aspergillus, isolated and identified as a hitherto undescribed mcroorganism, has been designated MF-4833 in the culture collection of Merck and Co., Inc., Rahway, N.J. and a culture thereof has been placed on permanent deposit with the American Type Culture Collection, 12301 Parklawn Drive, Rockville, MD 20852, and has been assigned accession No. ATCC No. 20541. Another sample, of a similar organism, designated MF -4845 in the Merck culture collection, has likewise been placed on deposit and has been given the accession number ATCC 20542. The latter organism is the one giving the better yield. Although the use of these is described in connection with the process of this invention, other organisms of the genus Aspergillus including mutants of the above ones are also capable of producing MSD803 and their use is contemplated in carrying out the process of this invention.

The morphological characteristics of the microorganisms MF-4833 and MF-4845 have been found to be those of the genus Aspergillus. Using the criteria specified in the standard authority "Manual of the Aspergilli", Charles Thom and Kenneth B. Rasper, published by the Williams and Wilkins Company, Baltimore, Md., 1945, and by comparison with known species, it has been determined that both strains are *Aspergillus terreus*.

The culture of these organisms to produce MSD803 is carried out in aqueous media such as those employed for the production of other fermentation products. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, ryes, cornstarch, corn meal and the like can be used either alone or in combination as sources of assimilable carbon in the nutrient medium. The exact quantity of the carbohydrate source of sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include for example, yeast hydrolysates, primary yeast, soybean meal, cottonseed flour, hydrolysates of casein, corn steep liquor, distiller's solubles or tomato paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and are not intended to be limitative. Specifically, the carbon sources used in the culture media to produce MSD803 included dextrose, dextrin, oat flour, oatmeal, molasses, citrate, soybean oil, glycerol, malt extract, cod liver oil, starch, ethanol, figs, sodium ascorbte and lard oil. Included as nitrogen sources were peptonized milk, autolyzed yeast, yeast RNA, tomato paste, casein, primary yeast, peanut meal, distillers solubles, corn steep liquor, soybean mean, corn meal, NZ amine, beef extract, aspargine, cottonseed meal and ammonium sulfate. The major ionic components were $CaCO_3$, $KH_2PO_4$, $MgSO_4.7H_2O$ and $NaCl$ and small amounts of $CoCl_2.6H_2O$ and traces of Fe, Mn, Mo, B and Cu were also present.

The fermentation is carried out at temperatures ranging from about 20° to 37° C.; however, for optimum results it is preferable to conduct the fermentation at temperatures of from about 22° to 30° C. The pH of the nutrient media suitable for growing the Aspergillus culture and producing MSD803 can vary from about 6.0 to 8.0.

Although the novel compound is produced by both surface and submerged culture, it is preferred to carry out the fermentation in the submerged state. A small scale fermentation is conveniently carried out by inoculating a suitable nutrient medium with the Aspergillus culture and, after transfer to a production medium, permitting the fermentation to proceed at a constant temperature of about 28° C. on a shaker for several days.

The fermentation is initiated in a sterilized flask of medium via one or more stages of seed development. The nutrient medium for the seed stage may be any suitable combination of carbon and nitrogen sources. The seef flask is shaken in a constant temperature chamber at about 28° C. for 2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as for example, from 3 to 5 days while agitating and/or aerating the nutrient medium and maintaining the temperature at about 28° C. This method of producing MSD803 is particularly suited for the preparation of large quantities.

The compound is conveniently isolated from the fermentation broth as the lactone. However, MSD803 is present in the fermentation broth largely as the hydroxycarboxylate (open lactone) form. It is possible to isolate this form and its salts. Alternatively, the lactone form can be hydrolyzed with bases such s NaOH to yield the corresponding salts such as the sodium salts. The use of bases with the pharmaceutically acceptable cations affords salts of these cations. Careful acidification of the salts affords the hydroxy acid form. Conversely, the hydroxy acid can be converted to the lactone form at acidic pH. Opening the lactone, under catalysis, with methanol, ethanol, propanol, or butanol or with phenyl, dimethylamino, or acetylamino alkanols yields the corresponding esters of this invention.

The physico-chemical properties of MSD803 in its lactone form are summarized as follows:

| 1. | Melting point | 170–171° |
|---|---|---|
| 2. | Molecular Weight (mass spectrum) | 404 |
| 3. | Formula | $C_{24}H_{36}O_5$ |
|  | (found by mass spectrometry | 404.2555 |
|  | calculated) | 404.2563 |
| 4. | UV Spectrum |  |
|  | (in acetonitrile) | Maxima |
|  |  | 230.5 nm with E% 505.7 |
|  |  | 237.5 nm with E% 576.6 |
|  |  | 246 nm with E% 395.2 |

5. $^{13}C$ NMR chemical shifts. The spectrum has been recorded in $CDCl_3$ solution (20.1 mg in 0.35 ml). Chemical shifts are given relative to internal tetramethylsilane at zero ppm; under the experimental conditions the solvent ($CDCl_3$) signal appears centered at 70.0 ppm. In agreement with mass spectral data 24 carbon atoms are observed; their chemical shifts are: 11.5, 13.6, 16.0, 22.6, 24.1, 26.6, 27.2, 30.5, 32.8, 35.9, 36.4, 37.1, 38.4, 41.3, 62.4, 67.8, 76.4, 128.4, 129.7, 131.7, 133.2, 170.8 and 177.2 ppm.

6. $^1H$ NMR Spectrum

The spectrum was recorded in CDCl₃ solution and chemical shifts are shown in FIG. 1 in ppm relative to internal tetramethylsilane at zero ppm.

7. IR Spectrum

The infra red spectrum was recorded in a KBr pallet preparation of a sample. It is shown in FIG. II.

8. Optical rotation.

The specific optical rotation $[\alpha]_D^{25} = 320.7°$ has been determined on a solution of 5.30 mg/ml CH₃CN. This value has been obtained by measuring at the sodium-D-line wave length.

On the basis of these and other data, the structure of the product believed with a considerable degree of certainty to have the chemical structure;

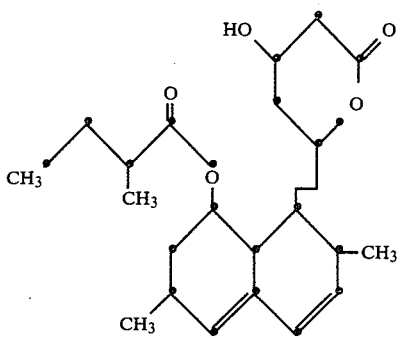

This invention can be illustrated by the following examples.

EXAMPLE 1

A. Fermentation

A tube of lyophilized culture MF-4833 is opened aseptically and the contents suspended in an unbaffled 250 ml Erlenmeyer flask (seed flask) containing approximately 20 ml of medium A. Medium A has the following composition:

| Medium A | |
|---|---|
| Corn steep liquor | 10 g |
| Tomato paste | 80 g |
| Oatmeal | 20 g |
| Glucose | 20 g |
| Trace Element Mix No. 2 | 20 g |
| Distilled water | 1000 ml |
| pH 6.8 with NaOH | |
| Trace Element Mix No. 2 | |
| FeSO₄ . 7H₂O | 1000 mg |
| MnSO₄ . 4H₂O | 1000 mg |
| CuCl₂ . 2H₂O | 25 mg |
| CaCl₂ . 2H₂O | 100 mg |
| H₃BO₃ | 56 mg |
| (NH₄)₆Mo₇O₂₄ . 4H₂O | 19 mg |
| ZnSO₄ . 7H₂O | 200 mg |
| Distilled Deionized Water | 1000 mg |

The inoculated flask is incubated for 48 hours at 28° C. on a 220 rpm shaker (2 inch throw). Two unbaffled 2 liter Erlenmeyer flasks each containing 500 ml of medium B are then each inoculated with 10 ml per flask of the growth from the seed flask. Medium B has the following composition:

| Medium B | |
|---|---|
| Tomato paste | 20 g |
| Primary yeast | 10 g |
| CPC Starch | 20 g |
| CoCl₂ . 6H₂O | 5 mg |
| Distilled water | 1000 ml |
| pH 7.2-7.4 with NaOH | |

These two inoculated flasks are incubated for 96 hours at 28°. One flask is incubated without agitation. The other flask is incubated on a 150 rpm shaker (2" throw). After 96 hours, the contents of each flask is set aside for isolation of the product.

B. Isolation

The whole broth is centrifuged for 20-30 min. Solids are saved for extraction. The supernatant liquid (pH 6-8) is charged to a 950 ml bottle and 150 ml XAD-2 resin is added. Using an automatic Extractor, operating on a preset schedule, the mixture is stirred for 2 hours. The spent broth is then siphoned off and discarded. The resin is washed twice with 200 ml of deionized water and the washes were discarded. There then is added a charge of 300 ml of mixed solvent: isopropanol-ethyl acetate-dichloromethane 25-45-30. The mixture is stirred two hours. The solvent-resin slurry is filtered on a Buchner or sintered glass funnel and the resin is discarded. The filtrate broth solids are stirred with 100 ml acetone for ½ hour. The mixture is then centrifuged and the supernatant liquor is decanted. The combined filtrates are concentrated to 15 ml.

C. Testing

The filtrates were tested as inhibitors of HMG-CoA reductase enzyme by the method described by Beg, Stonik, Brewer and Bryan (1977 *FEBS Letters* 80 123 to 129) using enzymes prepared as described by Kleinsek, Rangatham and Porter (1977 *Proc. Nat. Acad. Sci.* 74 1431 to 1435). The positive test (over 90% inhibition at 20 micrograms per milliliter—an IC₅₀ of 2.3 micrograms per milliliter indicated the presence of a very potent inhibitor of sterol synthesis acting at the HMG-CoA reductase level.

EXAMPLE 2

A. A tube of lyophilized culture of an Aspergillus sp. MF-4833 is opened aseptically and the contents suspended in an unbaffled 250 ml Erlenmeyer flask (seed flask No. 1) containing 40 ml of medium C. Medium C has the following composition:

| Medium C | |
|---|---|
| Corn steep liquor | 5 g |
| Tomato paste | 40 g |
| Oatmeal | 10 g |
| Glucose | 10 g |
| Trace element Mix No. 2 | 10 g |
| Distilled water | 1000 ml |
| pH 6.8 with NaOH | |

This inoculated flask is incubated for 24 hours at 28° C. on a 220 rpm shaker (2 inch throw) for 24 hours. Eight more unbaffled 250 ml Erlenmeyer flasks (No. 2 seed flask) each containing 40 ml of medium C are then each inoculated with 2 ml per flask of the growth from seed flask No. 1. These eight No. 2 seed flasks are incubated for 24 hours at 28° C. on a 220 rpm shaker (2 inch throw). Twenty, two liter unbaffled Erlenmeyer flasks, containing 500 ml of medium B are then each inoculated with 14 ml per flask of the combined growth of the eight No. 2 seed flasks. These twenty flasks are incubated at 28°, without agitation for 11 days. After 11 days incubation, the contents of these twenty flasks are pooled.

B. 10.2 liters of whole broth, pH 6.0, was blended in a Waring blender to break up the heavy mycelial pads, centrifuged and the clear supernatant decanted. After filtration the 10 liters of filtrate was extracted with 3 liters of ethyl acetate, yielding 1820 ml of clear extract. A second extraction with 3 liters of ethyl acetate yielded 3350 ml of clear extract. The broth solids were extracted by stirring one hour with 2 liters of methanol and filtering to yield 2100 ml of filtrate.

Aliquots of these extracts were dried and sent for assay by the procedure of Example 1(C), with the following results:

| | Extract | |
|---|---|---|
| Volume (ml) | Total Solids (mg) | Total Units of Activity |
| 1820 | 1133 | 1,496,695 |
| 3350 | 787 | 314,900 |
| 2100 | 13.15 | 1,144,067 |

C. Gel Filtration

All of samples from the first two extracts in Example 2 (B) were combined, dissolved in methanol and filtered to remove insoluble solids. The 30 ml of filtrate was loaded onto a gel filtration column (2.5 cm×200 cm, 980 ml) packed with Sephadex LH-20 and the sample fractionated according to molecular size using methanol as solvent. With refractive index and U.V. recordings as guides, the best fractions were identified by bioassay.

| Total Solids (mg) | Total Units of Activity |
|---|---|
| Fraction 1 - 89 | 106,271 |
| Fraction 2 - 278 | 1,099,680 |
| Fraction 3 - 779 | 210,357 |

D. Separation and Purification

A sample from Fraction 2 above was prefiltered through a 1-gram bed of Waters Bondapak C18/Porasil B and eluted with five volumes of methanol. The methanol eluate was concentrated to 0.5 ml. This sample was chromatographed, over several runs, on a Waters $\mu$C18 column (3.9 mm×30 cm) with methanol:0.05 M ammonium phosphate, pH 2.9 (75:25), as the developing solvent. Fractions were scanned on a Beckman Spectrophotometer, and those showing absorption maxima at 236 nm, with shoulders at 229 nm and 245 nm were combined and concentrated under reduced pressure to an aqueous solution. The pH of the concentrate was adjusted to 6.5 with 2 M potassium hydroxide and the active components were extracted with ethyl acetate. The organic layer was dried and the residue dissolved in 0.3 ml methanol. The methanol solution was chromatographed as above and recycled. Cuts containing earlier eluting component were combined, concentrated to an aqueous solution and extracted with chloroform. The chloroform residue was taken up in methanol and the solvent evaporated under nitrogen. 3.5 mg. of dried product was obtained and identified as the open lactone form. Cuts containing the second component were combined and extracted with chloroform as above. 0.87 mg. of dried product were obtained and identified as the lactone.

Samples were sent for bioassay.

EXAMPLE 3

Best Mode of Fermentation of MF-4833

A tube of lyophilized culture of an Aspergillus sp. MF-4833 is opened aseptically and the contents suspended in an unbaffled 250 ml Erlenmeyer flask (seed flask) containing 40 ml of medium C. The inoculated flask is incubated for 48 hours at 28° C. on a 220 rpm shaker (2 inch throw). Two, 250 ml unbaffled Erlenmeyer flasks each containing 40 ml of medium D are then each inoculated with 2 ml per flask of the growth from the seed flask. Medium D has the following composition:

| Medium D | |
|---|---|
| Lactose | 20 g |
| Distillers solubles | 15 g |
| Autolyzed yeast | 5 g |
| Distilled water | 1000 ml |
| pH 7.0 with NaOH | |

These two inoculated flasks are incubated for 96 hours at 28° on a 150 rpm shaker (2 inch throw). After 96 hours incubation the contents of these two flasks is submitted for extraction by the procedure described in Example 2(B). Total production in these flasks is 1450–2000 units/ml.

EXAMPLE 4

A tube of lyophilized culture of an Aspergillus, MF 4845, is opened aseptically and the contents suspended in an unbaffled 250 ml Erlenmeyer flask (seed flask No. 1) containing 40 ml of medium C. The inoculated flask is incubated for 24–48 hours at 28° C. on a 220 rpm shaker (2 inch throw). A portion (approx. 0.5 ml) of this flask is then used to inoculate a slant tube containing medium E. Medium E has the following composition:

| Medium E | |
|---|---|
| Yeast Extract | 4 g |
| Malt Extract | 10 g |
| Dextrose | 4 g |
| Agar | 20 g |
| Distilled Water | 1000 ml |
| pH 7.0 with NaOH | |

The inoculated slant tube is incubated for 11 days at room temperature. It is then stored at −60° C. for 3–4 months. A portion of the contents of this slant is then suspended in an unbaffled, 250 ml Erlenmeyer flask (No. 2 seed flask) containing 40 ml of medium C. The inoculated flask is incubated for 24 hours at 28° C. on a 220 rpm shaker (2 inch throw). Six unbaffled 250 ml Erlenmeyer flasks (No. 3 seed flasks) containing 40 ml of medium C are then each inoculated with 2 ml per flask of the growth from the No. 2 seed flask. These six inoculated flasks are incubated for 48 hours at 28° on a 220 rpm shaker (2 inch throw). Six unbaffled two liter Erlenmeyer flasks containing 500 ml of medium F are each then inoculated with the contents of No. 3 seed flask. Medium F has the following composition:

| Medium F |
|---|

| | |
|---|---|
| Corn steep liquor | 15 g |
| CPC Starch | 20 g |
| Corn meal | 1 g |
| Soybean meal | 4 g |
| Glucose | 5 g |
| Soybean oil | 2.5 g |
| $(NH_4)_2SO_4$ | 4 g |
| $KH_2PO_4$ | 0.3 g |
| $CaCo_3$ | 6 g |
| Distilled Water | 1000 ml |
| pH 6.7 with NaOH | |

The inoculated flasks are incubated for 11 days without agitation at 28° C. After 11 days broth is delivered for extraction by the procedure of Example 2(B). Total production in these flaks is 1231 units/ml.

EXAMPLE 5

Best Mode of Fermentation with MF-4845

A tube of lyophilized culture of an Aspergillus, MF-4845, is opened aseptically and the contents suspended in an unbaffled 250 ml Erlenmeyer flask (seed flask) containing 40 ml of medium C. The inoculated flask is incubated for 30 hours at 28° on a 220 rpm shaker (2 inch throw). An unbaffled, 250 ml Erlenmeyer flask containing 40 ml of medium G is inoculated with 2 ml per flask of the growth from the seed flask. Medium G has the following composition:

| Medium G | |
|---|---|
| Dextrose | 45 g |
| Peptonized milk | 24 g |
| Autolyzed yeast | 2.5 g |
| Polyglycol P2000 | 2.5 ml |
| Distilled water | 1000 ml |
| pH 7.0 with NaOH | |

This inoculated flask is incubated for 120 hours at 28° C. on a 220 rpm shaker (2 inch throw). After 120 hours incubation, the contents of the flask is submitted for extraction by the procedure of Example 2 (B). Total production in this flask is 21,500 units/ml.

EXAMPLE 6

A. Large Scale Fermentation with MF4833

The medium used in each step of the fermentation comprised:

| | |
|---|---|
| Corn steep liquor | 5 g |
| Tomato paste | 40 g |
| Oat Flour | 10 g |
| Glucose | 10 g |
| Trace element solution | 10 ml |
| Distilled water | 1000 ml | adjusted to pH 6.8 with sodium hydroxide.

The trace element solution comprised:

| | |
|---|---|
| $FeSO_4 . 7H_2O$ | 1 g |
| $MnSO_4 . 4H_2O$ | 1 g |
| $CuCl_2 . 2H_2O$ | 25 mg |
| $CaCl_2$ | 100 mg |
| $H_3BO_4$ | 56 mg |
| $(NH_4)_6Mo_7O_{24} . 4H_2O$ | 19 mg |
| $Zn SO_4 . 7H_2O$ | 200 mg |
| distilled water | 1 liter |

All mediums were checked for sterility before innoculation with a microorganism.

To a 250 ml non-baffled Erlenmeyer flask was charged 40 ml of medium and the contents of one tube of lyophillized organism MF 4833. It was then shaken for 24 hours at 28° C. on a rotary shaker at 220 rpm. New flasks were then charged with 40 ml of medium and 1 ml of the first flasks' contents and were shaken an additional 24 hours at 28° C. A 2 liter flask was then charged with 400 ml of medium and 10 ml of the second stage fermentation mixture and this too was shaken for 24 hours at 28° C.

A 200 gallon stainless steel fermentation vat was then charged with 501 liters of a medium comprising:

| | |
|---|---|
| lactose | 2% wt/vol |
| distiller solubles | 1.5% wt/vol |
| autolyzed yeast | 0.5% wt/vol |
| Polyglycol P2000 | 0.25% wt/vol | whose pH was adjusted to 7.0. This was sterilized 15 minutes at 121° C. One liter of the third stage above was then charged and the mixture was incubated at 130 rpm at 28° C. for 96 hours with an air flow of 10 cfm.

B. Isolation of MSD803

About 37.5 lbs. (¾ bag) of a siliceous filter aid was added to 110 gal. whole broth from the culture of MF-4833 described above and the mixture was filtered through an 18-inch filter press. The clarified filtrate, (pH 6.6) was adjusted to pH 4.0 by careful addition of 450 ml of concentrated hydrochloric acid, and extracted by agitation with about one-third volume (36 gal.) of ethyl acetate. After separation, the upper solvent layer was removed, and the water phase gain extracted with ethyl acetate (38 gal.) in a similar fashion. After separation, the two extracts were combined and back-washed by agitation with about twelve gallons of water. After separation, the ethyl acetate solution was concentrated under vacuum at a temperature below 30° C., first in a stirred kettle, and finally in a rotary vacuum evaporator to a residual volume of slightly less than one gallon.

Approximately 1 gal. (3800 ml) of ethyl acetate concentrate from the preceding extraction was further concentrated in a rotary evaporator (ca 10 mm, 40° C. bath) to a syrup and was then concentrated twice more, after addition of about one liter of methylene chloride in two portions, to free the syrup of polar solvent. The final oil of about 300 ml which contained about 250 g of solids by dry weight determination, was made up to about 750 ml with ethyl acetate methylene chloride (30/70; v/v) and 200 g of silica gel was added and mixed in to form a slurry. This was layered over the top of a 14 cm by 36 cm column bed holding 2.5 kg of the same silica gel, in about 7.5 l volume, which has been packed as a slurry in the same solvent mixture. Development with the same solvent was continued until 3 liters of effluent was taken off as forerun.

Development with ethyl acetate-methylene chloride (50/50; v/v) was begun, taking 800 ml effluent fractions. Twelve fractions were taken, then 100% ethyl acetate elution was begun, and after seven more fractions, 100% acetone elution was begun. Fractions four through twenty-four were assayed for bio-activity in the HMG-CoA Reductase inhibition assay referred to in Example 1. Substantial activity was found in fractions 7 through 11. Peak activity was found in fraction 8. It was concentrated to an oil for further purification; dry wt. by solids determination was 9.0 gm.

Fraction 8 from the silica gel column was triturated with 50 ml methylene chloride and filtered; the dried filter cake weighed 4.9 gm. The filtrate was charged to a 2-inch I.D. by 1-meter long column filled with Sephadex LH-20 dextran gel (Pharmacia) swollen and equilibrated in methylene chloride, and the column was eluted with methylene chloride at a rate of 15 ml/min. MSD803 is eluted between 0.64 and 0.81 column volumes. Solvent was removed from this peak leaving a slightly brown residue weighing approximately 0.290 gm. 213 mg. of this residue was taken up in 1.5 ml of $CH_2Cl_2$—$CH_3CN$ (65-35), charged to a prepacked and equilibrated silica gel column (EM LOBAR Size B) and eluted with $CH_2Cl_2$—$CH_3CN$ (65-35) at 5 ml/min. Evaporation of solvent from the peak eluting between 235 and 360 ml of eluant left 121 mg of crystalline product, m.p. 155°-160° C. HPLC of this material on a EM RP 18 reverse-phase analytical column (E Merck HIBAR II, Cat. No. 906046) using 0.05 M sodium phosphate pH 3.0-acetonitrile 45-55 as eluant at 2 ml/min. showed a characteristic uv absorbing peak at 11 min.

Eighty-two mg of this material was recrystallized from 0.6 ml of absolute ethanol, then again from 0.4 ml of the same solvent to afford, after drying over-night in a desiccator over $P_2O_5$, 40 mg of white feathery crystals. Analytical HPLC on the system described above gave a single sharp peak at 11 minutes elution time. After further recrystallizations, a melting point of 170°-171° C. was obtained.

The product was identified by spectra, etc., as the lactone form of MSD803. This material, in the in vitro HMG-CoA reductase test (of Example 1) gave an 1 $C_{50}$ of 0.01 micrograms per milliliter.

EXAMPLE 7

Salts of MSD803

To a solution of 40 mg the product of Example 6 in 2 ml of ethanol is added 1 ml of aqueous NaOH ($10^{-4}$ moles; 1 equivalent). After one hour at room temperature, the mixture is taken to dryness in vacuo to yield the sodium salt of the free acid form of MSD803.

In like manner the potassium salt is prepared using one equivalent of potassium hydroxide and the calcium salt using one-half equivalent of CaO. Other pharmaceutically acceptable salts are likewise prepared using equivalent quantities of the appropriate base.

EXAMPLE 8

Preparation of Free Hydroxy Acid of MSD803

The sodium salt produced in Example 7 is redissolved in 2 ml of ethanol-water (1:1) and added to 10 ml of 0.1 N hydrochloric acid from which the liberated hydroxy acid is extracted with ethyl acetate. The latter solvent is washed once with water, dried and removed in vacuo with a bath temperature not exceeding 30°. The hydroxy acid derived slowly reverts to the lactone on standing.

EXAMPLE 9

To a solution of 4 mg of the product of Example 6 in 1 ml of absolute ethanol is added 0.1 ml 0.1 M sodium ethoxide in absolute ethanol. This solution is allowed to stand at room temperature for one hour, is then diluted into water and extracted twice with water, the ethyl acetate dried over anhydrous sodium sulfate is removed in vacuo to yield the ethyl ester of MSD803.

In like manner, by the use of equivalent amounts of methanol, propanol, butanol, isobutanol, t-butanol, amylalcohol, isoamylalcohol, 2-dimethylaminoethanol, benzylalcohol, phenethanol, 2-acctamidoethanol and the like, the corresponding esters are obtained.

What we claim is:

1. A process of producing a compound of the formula:

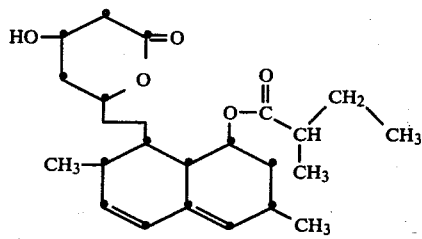

or its corresponding free acid which comprises fermenting a microorganism of the genus *Aspergillus terreus* and isolating the product thereof.

2. The process of claim 1 in which said microorganism is one deposited in the American Type Culture Collection with accession number 20541 or 20542.

3. The process of claim 1 in which the said isolation comprises extraction of a clarified aqueous solution of said fermentation mixture with a solvent followed by chromatography.

* * * * *